(12) United States Patent
Zhao et al.

(10) Patent No.: US 7,433,037 B2
(45) Date of Patent: *Oct. 7, 2008

(54) SYSTEM FOR MEASURING PERIODIC STRUCTURES

(75) Inventors: Guoheng Zhao, Milpitas, CA (US); Kenneth P. Gross, San Carlos, CA (US); Rodney Smedt, Los Gatos, CA (US); Mehrdad Nikoonahad, Menlo Park, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/458,934

(22) Filed: Jul. 20, 2006

(65) Prior Publication Data

US 2006/0290931 A1 Dec. 28, 2006

Related U.S. Application Data

(63) Continuation of application No. 11/016,148, filed on Dec. 17, 2004, now abandoned, which is a continuation of application No. 10/748,975, filed on Dec. 29, 2003, now abandoned, which is a continuation of application No. 09/742,029, filed on Dec. 20, 2000, now Pat. No. 6,721,052.

(51) Int. Cl.
*G01B 11/04* (2006.01)
*G01J 4/00* (2006.01)

(52) U.S. Cl. ..................... 356/369; 356/636

(58) Field of Classification Search ........... 356/369, 356/636, 367

See application file for complete search history.

(56) References Cited

U.S. PATENT DOCUMENTS 5,198,875 A 3/1993 Bazin et al.
(Continued)

OTHER PUBLICATIONS

International Search Report for PCT/US01/49259 mailed Feb. 18, 2001.

*Primary Examiner*—L. G. Lauchman
(74) *Attorney, Agent, or Firm*—Davis Wright Tremaine LLP

(57) ABSTRACT

A periodic structure is illuminated by polychromatic electromagnetic radiation. Radiation from the structure is collected and divided into two rays having different polarization states. The two rays are detected from which one or more parameters of the periodic structure may be derived. In another embodiment, when the periodic structure is illuminated by a polychromatic electromagnetic radiation, the collected radiation from the structure is passed through a polarization element having a polarization plane. The element and the polychromatic beam are controlled so that the polarization plane of the element are at two or more different orientations with respect to the plane of incidence of the polychromatic beam. Radiation that has passed through the element is detected when the plane of polarization is at the two or more positions so that one or more parameters of the periodic structure may be derived from the detected signals. At least one of the orientations of the plane of polarization is substantially stationary when the detection takes place. To have as small a footprint as possible, one employs an optical device that includes a first element directing a polychromatic beam of electromagnetic radiation to the structure and a second optical element collecting radiation from the structure where the two elements form an integral unit or are attached together to form an integrated unit. To reduce the footprint, the measurement instrument and the wafer are both moved. In one embodiment, both the apparatus and the wafer undergo translational motion transverse to each other. In a different arrangement, one of the two motions is translational and the other is rotational. Any one of the above-described embodiments may be included in an integrated processing and detection apparatus which also includes a processing system processing the sample, where the processing system is responsive to the output of any one of the above embodiments for adjusting a processing parameter.

17 Claims, 11 Drawing Sheets

U.S. PATENT DOCUMENTS

| | | |
|---|---|---|
| 5,438,415 A | 8/1995 | Kazama et al. |
| 5,517,312 A | 5/1996 | Finarov |
| 5,607,800 A | 3/1997 | Ziger |
| 5,739,909 A | 4/1998 | Blayo et al. |
| 5,764,365 A | 6/1998 | Finarov |
| 5,793,480 A | 8/1998 | Lacey et al. |
| 5,867,276 A | 2/1999 | McNeil et al. |
| 5,872,632 A | 2/1999 | Moore |
| 5,910,841 A | 6/1999 | Masao |
| 5,963,329 A | 10/1999 | Conrad et al. |
| 6,020,966 A | 2/2000 | Ausschnitt et al. |
| 6,100,985 A | 8/2000 | Scheiner et al. |
| 6,134,011 A | 10/2000 | Klein et al. |
| 6,522,406 B1 | 2/2003 | Rovira et al. |
| 6,710,876 B1 | 3/2004 | Nikoonahad et al. |
| 6,713,753 B1 | 3/2004 | Rovira et al. |
| 6,721,052 B2 | 4/2004 | Zhao et al. |
| 7,009,704 B1 | 3/2006 | Nikoonahad et al. |
| 7,115,858 B1 | 10/2006 | Holden et al. |
| 2002/0018217 A1 | 2/2002 | Weber-Grabau et al. |

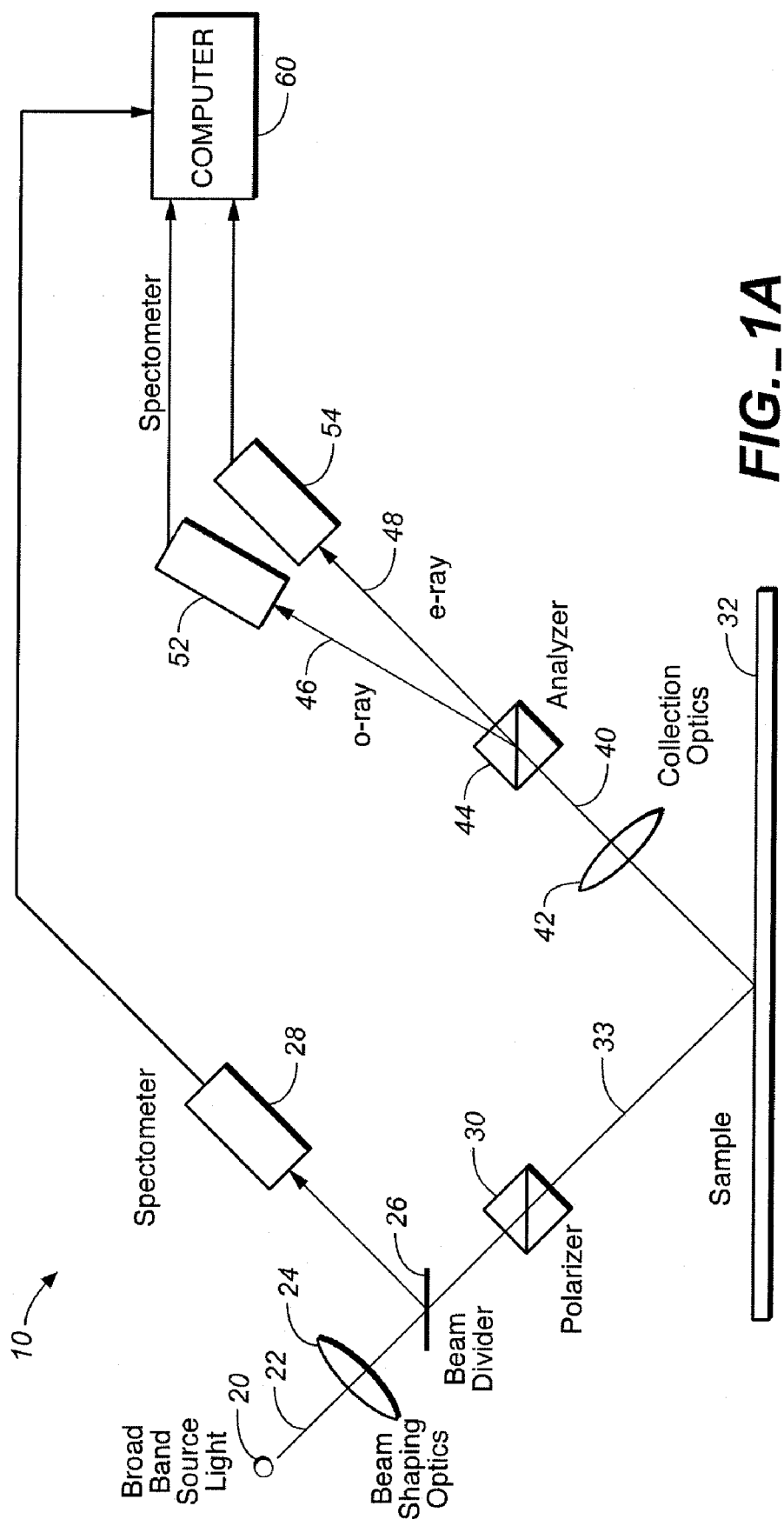
FIG._1A

SYSTEM FOR MEASURING PERIODIC STRUCTURES

CROSS-REFERENCE TO RELATED APPLICATIONS

This application is a continuation of application Ser. No. 11/016,148, filed Dec. 17, 2004 now abandoned; which is a continuation of application Ser. No. 10/748,975, filed Dec. 29, 2003, now abandoned; which is a continuation of application Ser. No. 09/742,029, filed Dec. 20, 2000, now U.S. Pat. No. 6,721,052. These applications are incorporated in their entirety by reference as if fully set forth herein.

BACKGROUND OF THE INVENTION

This invention relates in general to optical techniques for measuring periodic structures, and in particular to an improved spectroscopic diffraction-based metrology system for measuring periodic structures, such as grating-type targets on semiconductor wafers.

In conventional techniques, optical microscopes have been used for measuring the critical dimension ("CD") for semiconductor lithographic processes. However, as the CD becomes smaller and smaller, it cannot be resolved at any practical available optical wavelengths in optical microscopy. Scanning electron microscope technology has extremely high resolution. However, this technology inherently requires large capital expenditures and heavy accessory equipment such as vacuum equipment, which makes it impractical for integration with lithographic processes. Two-theta scatterometers face similar practical challenges for integration, as they require mechanical scanning over a wide range of angles. For this reason, they are slow and difficult to integrate with process equipment.

Ellipsometric techniques have also been used for CD measurements. In U.S. Pat. No. 5,739,909, for example, Blayo et al. describe a method of spectroscopic ellipsometry adapted to measure the width of features in periodic structures. While ellipsometric methods may be useful for some applications, such methods have not been able to measure reflectances from the periodic structures.

None of the above-described techniques is entirely satisfactory. It is therefore desirable to provide an improved technique for measuring periodic structures where the above-described difficulties are alleviated.

SUMMARY OF THE INVENTION

In many of the diffraction-based metrology or ellipsometric techniques for measuring the critical dimension, theoretical models employing libraries or non-linear regression are employed to find the critical dimension or other parameters of the periodic structure. Where the periodic structure measured is topographically complex, it may be necessary to measure more than one radiation parameter to get adequate information for the modeling process. Where the periodic structure is simple, however, the measurement of a single radiation parameter may be adequate. The use of fewer radiation parameters in the modeling process reduces the calculation time required so that the critical dimension and other parameters of the structure can be found quickly. The embodiments of this invention are simple in construction and flexible and may be used for measuring one or more radiation parameters from the radiation diffracted by the periodic structure.

In one embodiment of the invention, when the structure is illuminated by polychromatic electromagnetic radiation, radiation from the structure is collected and divided into two rays having different polarization states. The two rays are detected, from which one or more parameters of the periodic structure may be derived. In another embodiment, when the periodic structure is illuminated by polychromatic electromagnetic radiation, the collected radiation from the structure is passed through a polarization element having a polarization plane. The element and the polychromatic beam are controlled so that the polarization planes of the element are at two or more different orientations with respect to the plane of incidence of the polychromatic beam. Radiation that has passed through the element is detected when the planes of polarization are at two or more positions so that one or more parameters of the periodic structure may be derived from the detected signals. At least one of the orientations of the plane of polarization is substantially stationary when the detection takes place.

When a device for measuring periodic structure parameters is employed in a production environment, such as when it is integrated with wafer processing equipment, it is desirable for the device to have as small a footprint as possible. One embodiment of the invention adapted for such environments employs an optical device that includes a first element directing a polychromatic beam of electromagnetic radiation to the structure and a second optical element collecting radiation from the structure where the two elements form an integral unit or are attached together to form an integrated unit.

One way to reduce the footprint of the apparatus for measuring the periodic structure in a wafer processing environment is to move the apparatus relative to the wafer without moving the wafer itself. However, since the apparatus includes a number of components, it also has a significant size and footprint compared to that of the wafer. Furthermore, it may be cumbersome to control the sizable apparatus so that it can move in a two dimensional plane without moving the wafer. Thus, it is envisioned that both the apparatus for measuring the periodic structure and the sample (e.g. wafer) are caused to move. In one embodiment, translational motion of the apparatus and the wafer is caused where the two motions are transverse to each other. In a different arrangement, one of the two motions is translational and the other is rotational. This facilitates the handling of the motion of the apparatus while at the same time reduces the overall footprint.

Any one of the above-described embodiments may be included in an integrated processing and detection apparatus which also includes a processing system processing the sample, where the processing system is responsive to the output of any one of the above embodiments for adjusting a processing parameter.

BRIEF DESCRIPTION OF THE DRAWINGS

FIG. 1A is a schematic view of an apparatus for measuring one or more parameters of the periodic structure to illustrate one embodiment of the invention.

For simplicity in description, identical components are labeled by the same numerals in this application.

DETAILED DESCRIPTION OF THE EMBODIMENTS

Figure 1B:
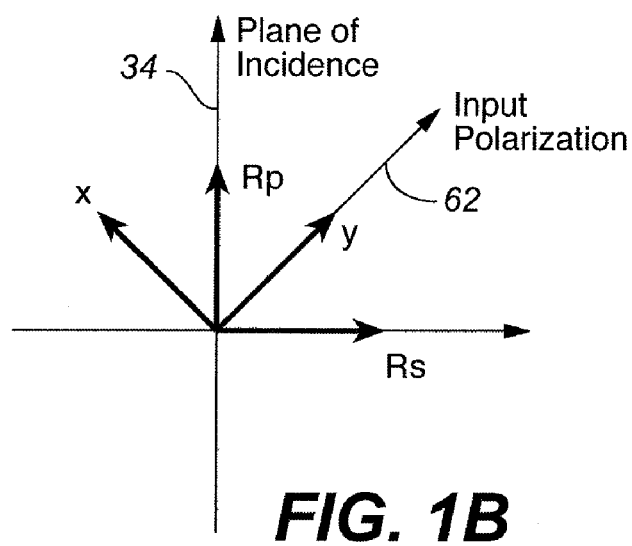
FIG. 1B is a schematic diagram of the plane of incidence and the planes of polarization of the polarizer and analyzer of FIG. 1A to illustrate the operation of the apparatus of FIG. 1A.

As shown in FIG. 1, a broadband source of electromagnetic radiation 20 provides a polychromatic beam with wavelength components preferably from 180 to 1000 nm. In one embodiment, source 20 may be a xenon lamp. The beam 22 from source 20 is shaped by beam shaping optics 24. A portion of the beam 22 is diverted by a beam divider 26 to spectrometer 28 for monitoring intensity variations in beam 22 in order to normalize the results of detection. Beam 22 is polarized by a polarizer 30 and the polarized beam is directed to sample 32 to illuminate a periodic structure thereon. Preferably the plane of incidence 34 (see FIG. 1B) of beam 22 is perpendicular to the grating lines in the periodic structure of sample 32. Radiation originating from beam 22 that has been modified by sample 32, such as by reflection or transmission, is collected by collection optics 42 as a collected beam 40 and passed through an analyzer 44 which splits the collected radiation into two rays: an extraordinary ray or e-ray 46 and an ordinary ray or o-ray 48. Rays 46 and 48 are detected respectively by two spectrometers 52, 54 with outputs delivered to computer 60 along with the output of spectrometer 28 for determining one or more parameters of a periodic structure on sample 32.

Depending on the orientation of the polarizer 30 and analyzer 44, the e-ray and 0-ray contain information concerning two different radiation parameters. This is illustrated more clearly in reference to FIG. 1B. As shown in FIG. 1B, $R_s$ is the reflectance of the S component of beam 40 in the direction normal to the plane of incidence and $R_p$ is the reflectance of the P component of beam 40 within the plane of incidence 34 of beam 22. Assuming that polarizer 30 is oriented at an angle to the plane of incidence 34, where the angle is other than 0°, 90°, 180° or 270°, then beam 40 will contain both non-zero P components and S components. When a plane of polarization is said to be at an angle to the plane of incidence in this application, this angle can be of any value, including 0 and 180 degrees, unless stated otherwise. For example, beam 33 may have the input polarization along the plane 62 at an angle between 0 and 90 degrees to plane 34 in FIG. 1B. In such event, depending on the orientation of the plane of polarization of analyzer 44, different radiation parameters are measured. For example, if the plane of polarization of analyzer 44 is aligned with the plane of incidence 34 or perpendicular to the plane of incidence, then the components $R_p$, $R_s$ are measured, and the o-ray and e-ray would yield these two intensities. On the other hand, if the plane of polarization of the analyzer 44 is aligned with the input polarization plane 62 of beam 33, or is arranged to be perpendicular to plane 62, then one of the two rays 46, 48 would contain information concerning a signal X and the other ray would contain information concerning a signal Y (a vector perpendicular to signal X), where X and Y are defined as follows:

$$X=|r_s-r_p|^2$$

$$Y=|r_s+r_p|^2$$

where $r_s$ and $r_p$ denote the complex amplitude reflection coefficients for S and P polarizations, respectively, while $R_s$ and $R_p$ are the intensity reflection coefficients.

If the plane of polarization of polarizer 30 is in the plane of incidence 34 or perpendicular to it, it is not possible to measure both $R_p$ and $R_s$ simultaneously or measure X and Y simultaneously. This is true when the grating is perpendicular or parallel to the plane of incidence 34. In other words, where the grating is not perpendicular or parallel to the plane of incidence 34, it is possible to measure both $R_p$ and $R_s$ simultaneously or measure X and Y simultaneously irrespective of the plane of polarization of beam 33. It is also possible to remove polarizer 30 altogether so that the beam 22 illuminating sample 32 is unpolarized. In such event, in order to measure $R_s$ and $R_p$, the plane of polarization of analyzer 44 is preferably aligned with the plane of incidence 34 or perpendicular to it. Even where the plane of polarization of analyzer 44 is not parallel to the plane of incidence 34 or perpendicular to it, it is possible to measure quantities related to $R_s$ and $R_p$, which would be useful for measuring the structure.

Preferably the plane of polarization of the analyzer 44 is at an angle of 0, 45, 90, 135, 180, 225, 270 or 315 degrees from the plane of incidence 34, since this will optimize the amplitudes of the quantities measured. Where the plane of polarization of the analyzer 44 is at an angle of 0, 90, 180 or 270 degrees to plane 34, $R_p$, $R_s$ may be measured. Where the plane of polarization of the analyzer 44 is at an angle of 45, 135, 225 or 315 degrees to plane 34, X, Y may be measured. Where the polarizer 30 is oriented at one of the angles of 0, 45, 90, 135, 180, 225, 270 or 315 degrees from the plane of incidence 34, again the amplitudes of the quantities measured will be optimized.

After $R_p$, $R_s$, X, Y have been measured, it is then possible to derive other radiation parameters therefrom in computer 60, so that a more complete list of quantities that can be obtained from the measurement are the following:

$R_s$, $R_p$, $R_s-R_p$, $(R_s-R_p)/(R_s+R_p)$ $X=|r_s-r_p|^2$, $Y=|r_s+r_p|^2$ $X/Y$, $X-Y=-4|r_s||r_p|\cos\Delta$ $(X-Y)/(X+Y)=\sin 2\psi \cos\Delta$ $\cos\Delta$, $$\tan\psi = \left|\frac{r_p}{r_s}\right|$$

where $r_s$ and $r_p$ denote the complex amplitude reflection coefficients for S and P polarizations respectively, while $R_s$ and $R_p$ are the intensity reflection coefficients: $R_s=|r_s|^2$, $R_p=|r_p|^2$. $\Delta$ denotes the phase difference between reflected s- and p-polarized fields. The quantities $\tan\Psi$ and $\cos\Delta$ are ellipsometric parameters known to those in the art.

Figure 1C:
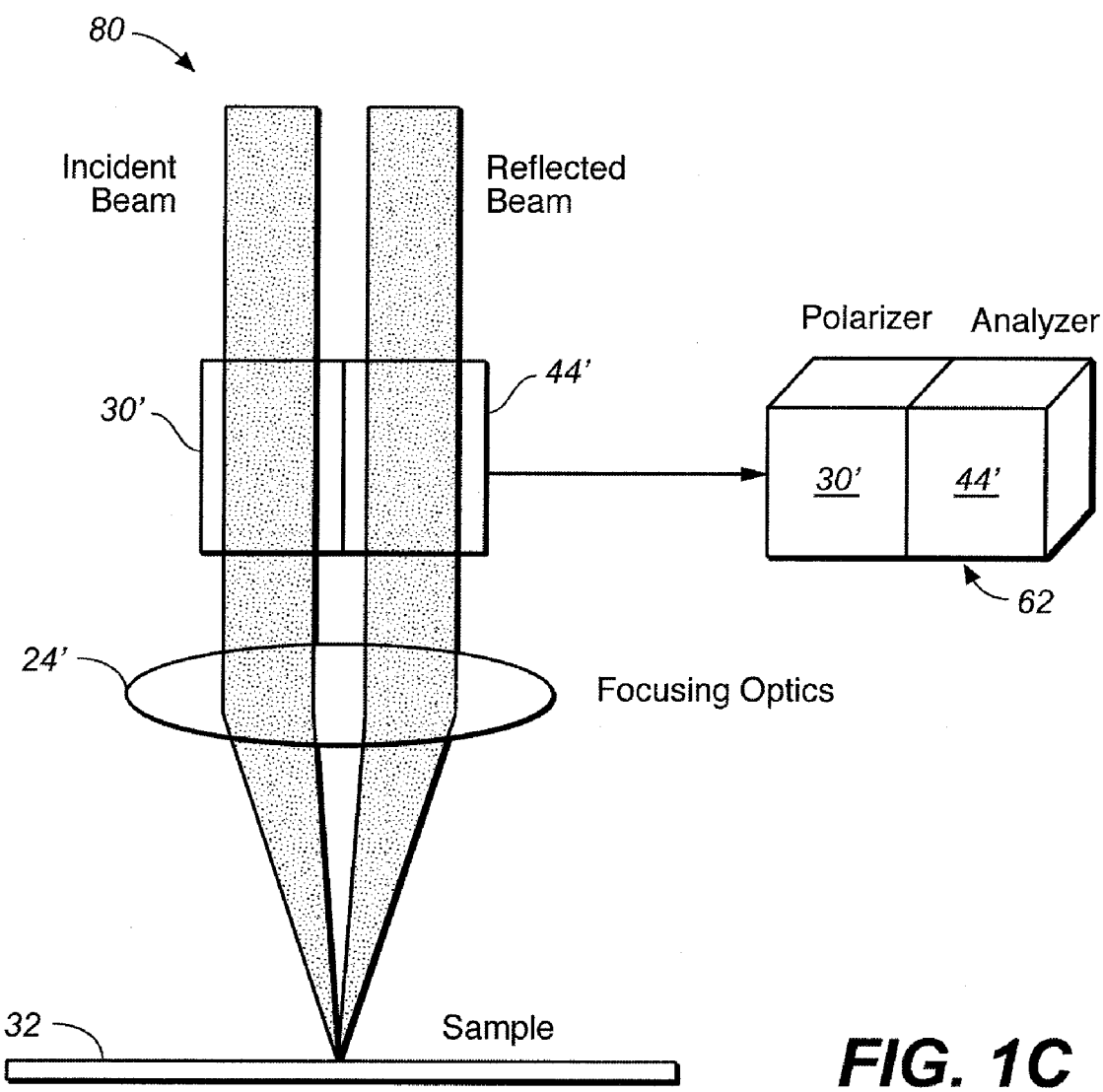
FIG. 1C is a schematic diagram of another apparatus for measuring one or more parameters of the periodic structure to illustrate an alternative embodiment of the invention particularly suitable in an integrated processing and detection tool to illustrate another embodiment of the invention.

The radiation parameter (Rs–Rp)/(Rs+Rp) has better sensitivity than Rs or Rp alone, since the reflectance difference (Rs–Rp) would tend to cancel out unwanted reflectance from isotropic film structures surrounding, over or underneath the grating targets when the illumination beam is at normal or near normal incidence. The ratio also reduces effects of intensity variations of the illumination beam on the measurement. By canceling out or reducing unwanted reflectance from isotropic film structures surrounding, over or underneath the grating targets, this feature renders the detection system more robust against stray reflectance around the grating target, and reduces the influence of thickness variations of films over or under the grating. Since the area available for the grating target is limited, where the optical system is not exactly aligned properly, some of the radiation from the illumination beam may be reflected from an area outside of the target, so that by using the computer 60 to calculate the reflectance difference, the measurement is much more robust despite optical misalignment errors, and reduces the influence of thickness variations of films over or under the grating. These variations are caused by process variations that introduce error in CD measurement. By measuring difference in reflectance, these unwanted effects tend to cancel to provide a more accurate CD measurement. As noted above, the output of spectrometer 28 may be used to normalize the output of spectrometers 52, 54 in order to eliminate the effects of intensity variation from source 20.

Where it is desirable to employ a compact system for detecting periodic structures, such as where the device is to be integrated with processing equipment, the configuration shown in FIG. 1C may be particularly useful. As shown in FIG. 1C, the incident beam 22 is passed through an element 30' which can be a polarizer, focused by optics 24' to sample 32. The zeroth order diffraction from the periodic structure on sample 32 is collected by focusing optics 24' and passed through an analyzer 44'. The functions of the polarizer 30' and analyzer 44' are similar to those of polarizer 30 and analyzer 44 of FIG. 1A described above. For a compact design, polarizer 30' and analyzer 44' may be a single integral unit or are separate elements attached together to form an integrated unit 62 so that the configuration of FIG. 1C is particularly compact. This allows the apparatus of FIG. 1C to have a particularly small footprint.

Figure 2:
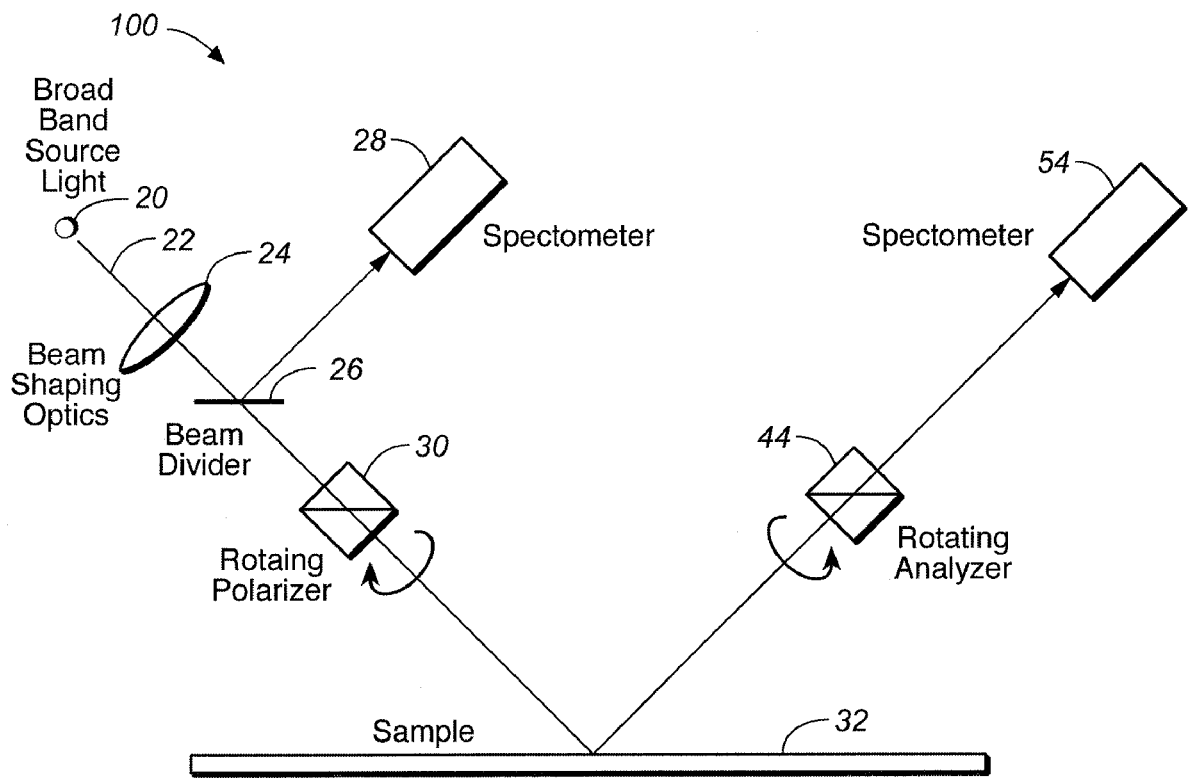
FIG. 2 is a schematic diagram of yet another measurement device for measuring one or more parameters of the periodic structure to illustrate yet another embodiment of the invention.

FIG. 2 is a schematic view of an apparatus 100 for measuring a periodic structure to illustrate another embodiment of the invention. For simplicity, the computer that processes the output of the two spectrometers 28, 54 has been omitted to simplify the drawing. System 100 differs from system 10 of FIG. 1A in that in system 100, either one or both of the polarizer 30 and analyzer 44 may be rotated whereas the polarizer and analyzer in system 10 of FIG. 1A are stationary and do not move. Furthermore, system 100 includes a single spectrometer for detecting the collected radiation instead of two spectrometers as in FIG. 1A. However, by rotating the polarizer 30 or analyzer 44, two or more radiation parameters may be detected. The operation of system 100 is different from an ellipsometer in that, for at least one measurement, the polarizer 30 and analyzer 44 are stationary and do not move. This permits system 100 to measure quantities such as $R_s$, $R_p$ whereas it would be extremely difficult for an ellipsometer to measure $R_s$, $R_p$ accurately.

System 100 operates under principles similar to that of FIG. 1A. Thus, if the plane of polarization of polarizer 30 is at an angle different from 0, 90, 180 and 270 degrees to the plane of incidence of beam 22, the plane of polarization of analyzer 44 may be oriented in the same manner as that described above in reference to FIG. 1B to measure at least one of the parameter values $R_s$, $R_p$, X, Y. Since only one spectrometer is used instead of two as in FIG. 1A, the quantities are measured sequentially rather than simultaneously as in the embodiment of FIG. 1A. Thus, in reference to FIG. 1B, if the plane of polarization of analyzer 44 is aligned with the plane of incidence 34 of beam 22, then the spectrometer would detect the radiation parameter $R_p$. Then analyzer 44 is rotated so that its plane of polarization is substantially normal to plane 34; at this stationary position of analyzer 44, the spectrometer 52 measures the radiation parameter $R_s$. The same can be said for the measuring of X, Y, where analyzer 44 is rotated so that its plane of polarization is substantially parallel and normal to plane 62, where the measurements are conducted sequentially rather than simultaneously. In other words, analyzer 44 may be sequentially oriented so that its plane of polarization is substantially at some of the angles of about 0, 45, 90, 135, 180, 225, 270 or 315 degrees to the plane of incidence 34, in order to measure one or more of the parameter values $R_s$, $R_p$, X, Y.

Figure 3:
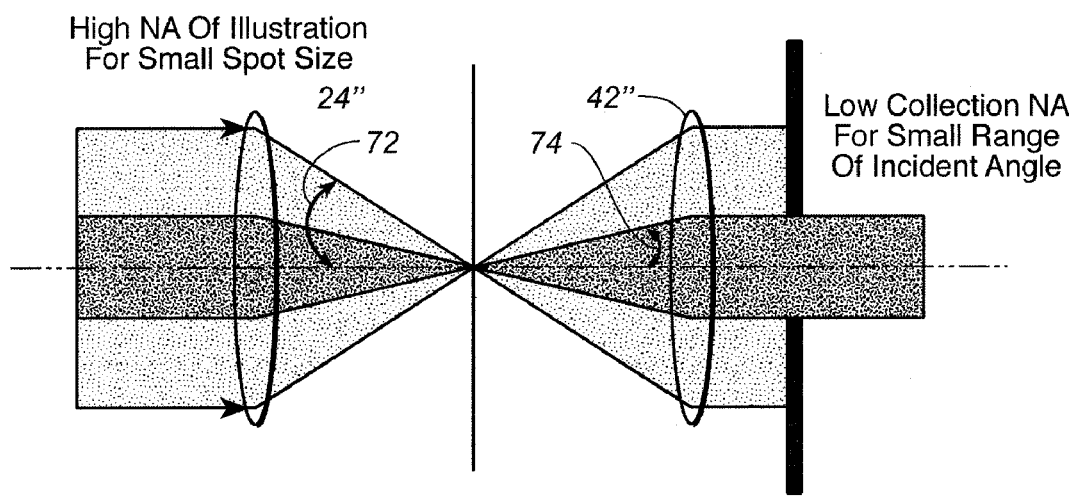
FIG. 3 is a schematic diagram of illumination and collecting optics employed in the different embodiments of this invention to illustrate an asymmetric numerical aperture for illumination and collection.

FIG. 3 is a schematic view of illumination optics 24" and collection optics 42" to illustrate another aspect of the invention. CD measurements require a dedicated grating-type target that is printed on the scribe line between dies on a semiconductor wafer. The area available for such target is typically limited so that the target size is typically kept to a minimum, such as around 25 microns square. Even a small percentage of light reflected from areas outside of the grating target can affect the measurement accuracy. For this reason, a relatively large focusing numerical aperture is employed to keep the energy of the illumination beam focused on the small target area. Thus, as shown in FIG. 3, the illumination numerical aperture 72 is relatively large. A large numerical aperture in the collection optics increases the computing time for modeling since the spectrum at more incident angles would need to be calculated. For this reason, it may be desirable to employ a small collection numerical aperture, such as aperture 74 shown in FIG. 3, for the collection optics. While FIG. 3 illustrates the collection optics in transmission mode, the same can be applied to reflection mode, such as those in FIGS. 1A, 1C and 2.

Figure 4A:
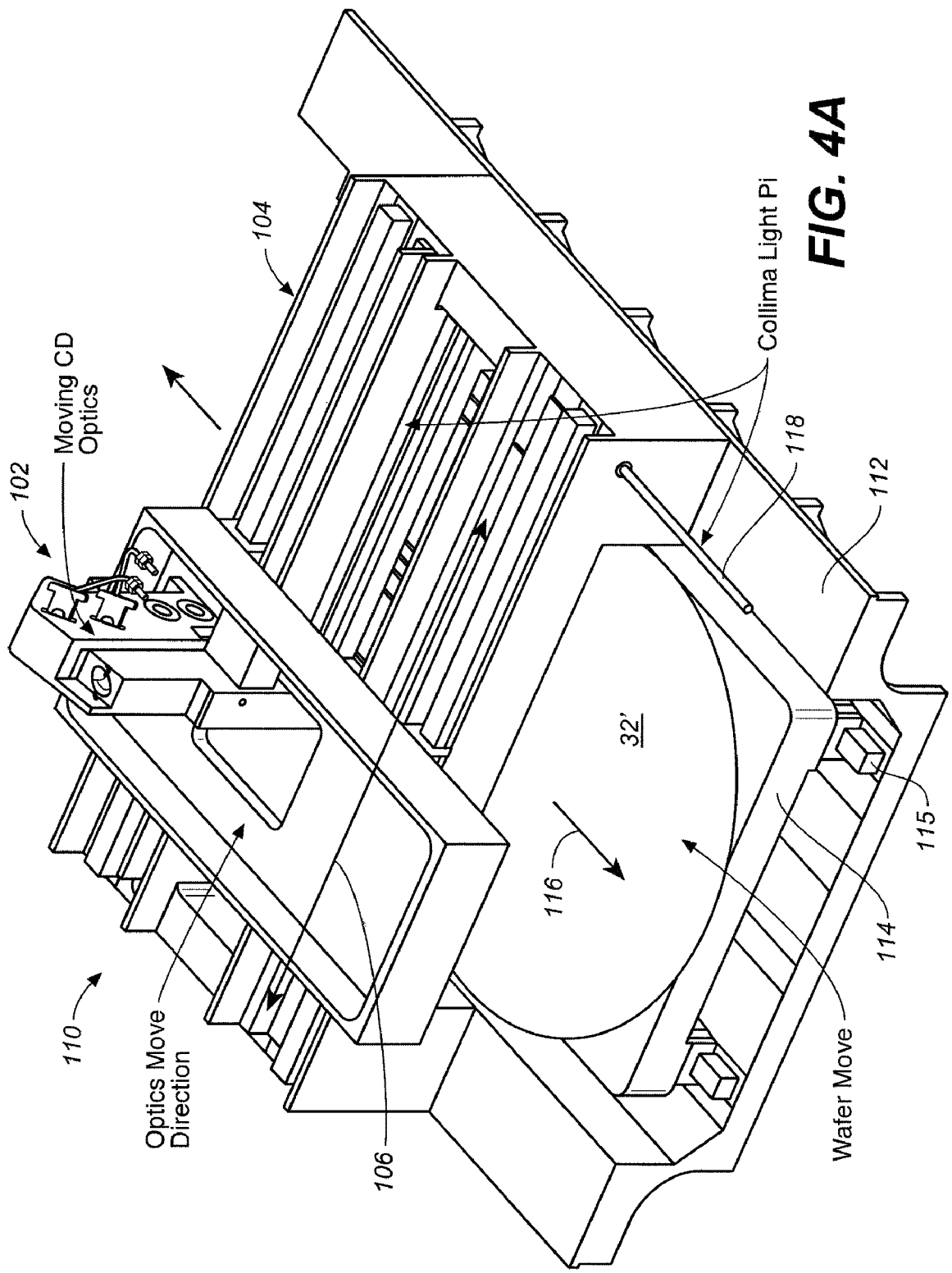
FIG. 4A is the perspective view of a semiconductor wafer and an apparatus for measuring periodic structures on the wafer and instruments for moving the apparatus and the wafer to illustrate yet another embodiment of the invention.

In another embodiment of the invention, both the apparatus and the wafer are moved relative to each other. Where the apparatus is moved in a translational motion along a straight line, such motion is easy to control despite the size and the number of components in the apparatus. Where the wafer is moved in the direction perpendicular to the motion of the apparatus, the footprint of the entire system can be reduced by making the dimension of the apparatus elongated along the direction of motion of the wafer, in order to minimize the dimension of the apparatus along the direction of its motion, in order to minimize footprint. This is illustrated in FIG. 4A. As shown in FIG. 4A, an optics head 102 is mounted onto a translation track 104 and a motor (not shown) causes head 102 to move along the track 104 along direction 106. Track 104 is attached onto supporting base 112, having tracks 115. The semiconductor wafer 32' is placed onto a chuck 114 which is caused by another motor (not shown) to move along track 115 along direction 116. Where directions 106, 116 are transverse to each other, such as perpendicular to each other, the movement of the optics head 102 and wafer 32' as described above would enable the optics head 102 to inspect the entire surface area of sample or wafer 32'. As will be evident from FIG. 4A, the optics head 102 is elongated in shape, with the elongated dimension substantially along direction 116, the direction of motion of wafer 32'. This reduces the dimension of optics head 102 in the direction of motion 106 of the head, thereby reducing the footprint required. Thus, as shown in FIG. 4A, the footprint of the entire assembly shown in FIG. 4A has the dimension along direction 106 substantially equal to the sum of the dimension of wafer 32' and optics head 102. The footprint of the assembly along direction 116 is substantially twice the dimension of wafer 32' along such direction.

Figure 4B:
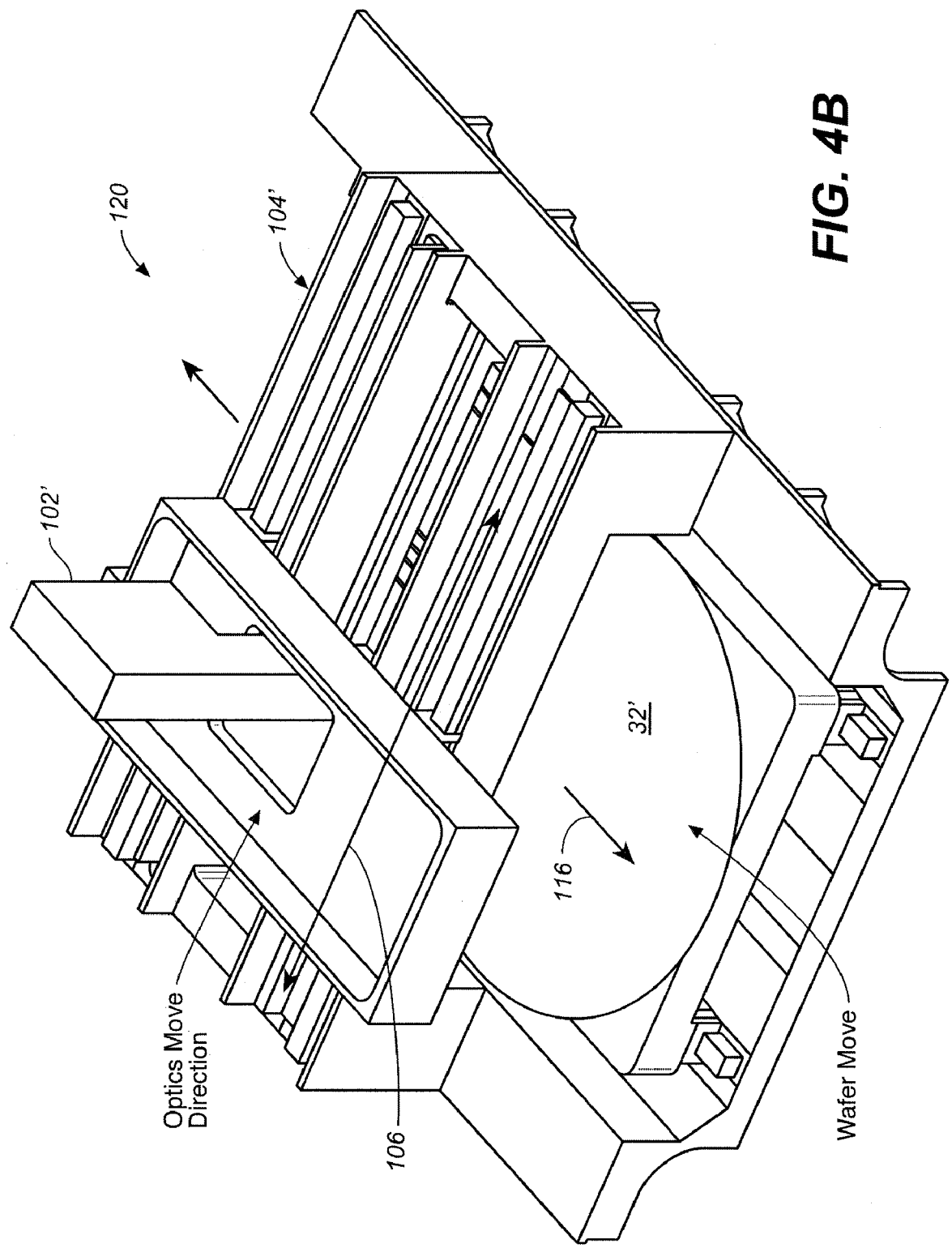
FIG. 4B is a perspective view similar to that of FIG. 4A except that the apparatus of FIG. 4B is self-contained in the optical head and includes a polychromatic electromagnetic radiation source.

FIG. 4B illustrates in perspective view an assembly 120 that is similar to assembly 110 of FIG. 4A, except that assembly 120, the optics head contains a radiation source and all collection optics and sensor components, so that it has no provision for an optical fiber leading to the optics head. In FIG. 4A, on the other hand, the optics head 102 does not include a source of radiation, so that an optical channel, such as an optical fiber 118, is employed to supply radiation to optics head 102. Track 104 has a passage therein to provide a conduit for the optical channel 118 to the optics head. In FIG. 4B, the optics head 102' contains a radiation source, so that track 104' does not need to provide the passage for an optical channel.

Figure 4C:
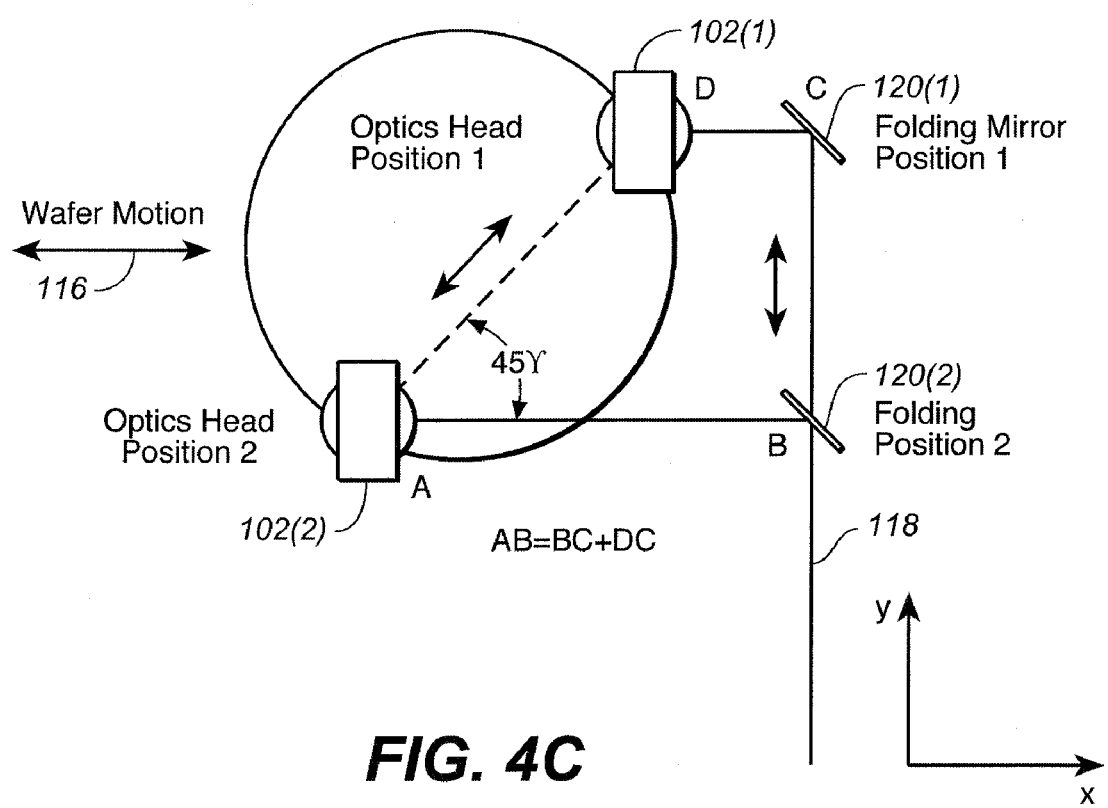
FIG. 4C is a schematic view of a semiconductor wafer and of optics arranged so that the optical path length remains substantially constant irrespective of the positions of the moving optics head relative to the wafer and illustrates yet another embodiment of the invention.

FIG. 4C is a schematic diagram of a semiconductor wafer and of optics arranged so that the optical path lengths to all positions of the optics head remain substantially constant irrespective of the position of the optics head relative to the wafer to illustrate yet another embodiment of the invention. In FIG. 4C, radiation used for inspection is supplied along an optical channel 118. When the optics head is at position 102(1) or D, radiation along channel 118 would reach the optics head 102 by reflection by means of folding mirror 120 (at position 120(1) or C) to the optics head. In other words, the optical path length would include the paths BC and CD. In the embodiment shown in FIG. 4C, the wafer is moved along direction 116 or one parallel to the x axis, and the optics head is moved along direction 122 substantially at 45 degrees to the x axis. The folding mirror is moved along the y axis at a speed such that the mirror and the optics head are maintained to be along a line parallel to the x axis or direction 116. Thus, after the optics head and the wafer are both moved so that the optics head is now at position 102(2) or A, and the mirror at position 120(2) or B, the optics head will receive radiation from channel 118 along a different optical path AB than it received when it was at position 102(1). Since the line AD is at 45 degrees to direction 116, the optical path length AB is equal to the sum of the path lengths BC+DC. If the optical beam along channel 118 is not collimated, any optical path difference depending on the positions of the optics head may cause complications in the measurement process. At a minimum, this may call for a calibration process which may be cumbersome. For this reason, in the embodiment of FIG. 4C, the optics for directing radiation from channel 118 to different positions of the optics head is designed so that the total optical path length remains substantially the same irrespective of the position of the optics head.

Figure 5:
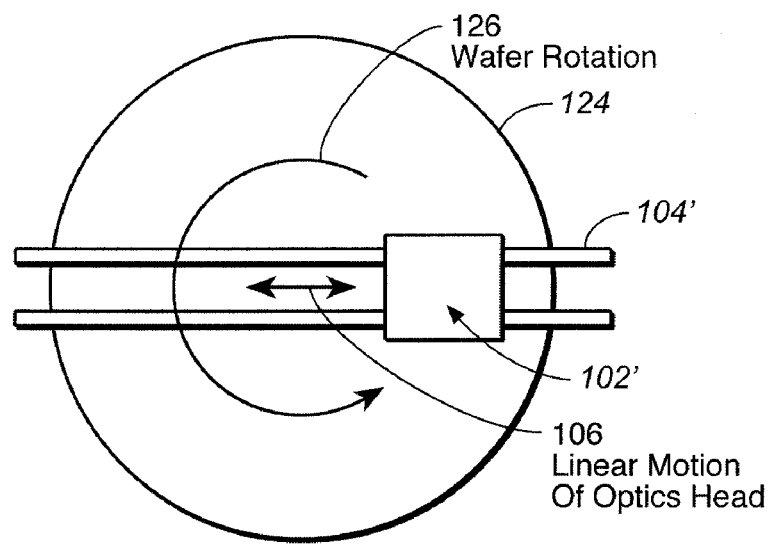
FIG. 5 is a schematic view of a system for moving the optics head along a straight line and for rotating the wafer.

In yet another embodiment, to further reduce the footprint of the system, the wafer is rotated while the apparatus for measuring the periodic structure is moved along substantially a straight line, so that the illumination beam from the apparatus scans a spiral path on the wafer. This is shown in FIG. 5. Thus, the optics head 102' is mounted onto a translation track 104' as in FIG. 4B and the optics head is moved along the track along direction 106 by a motor (not shown) as before. The wafer (not shown), however, is situated on top of a support 124 which is rotated along direction 126 by a motor (not shown). In this manner, the optics head 102' would have access to any location on the wafer for taking measurement.

Figure 6:
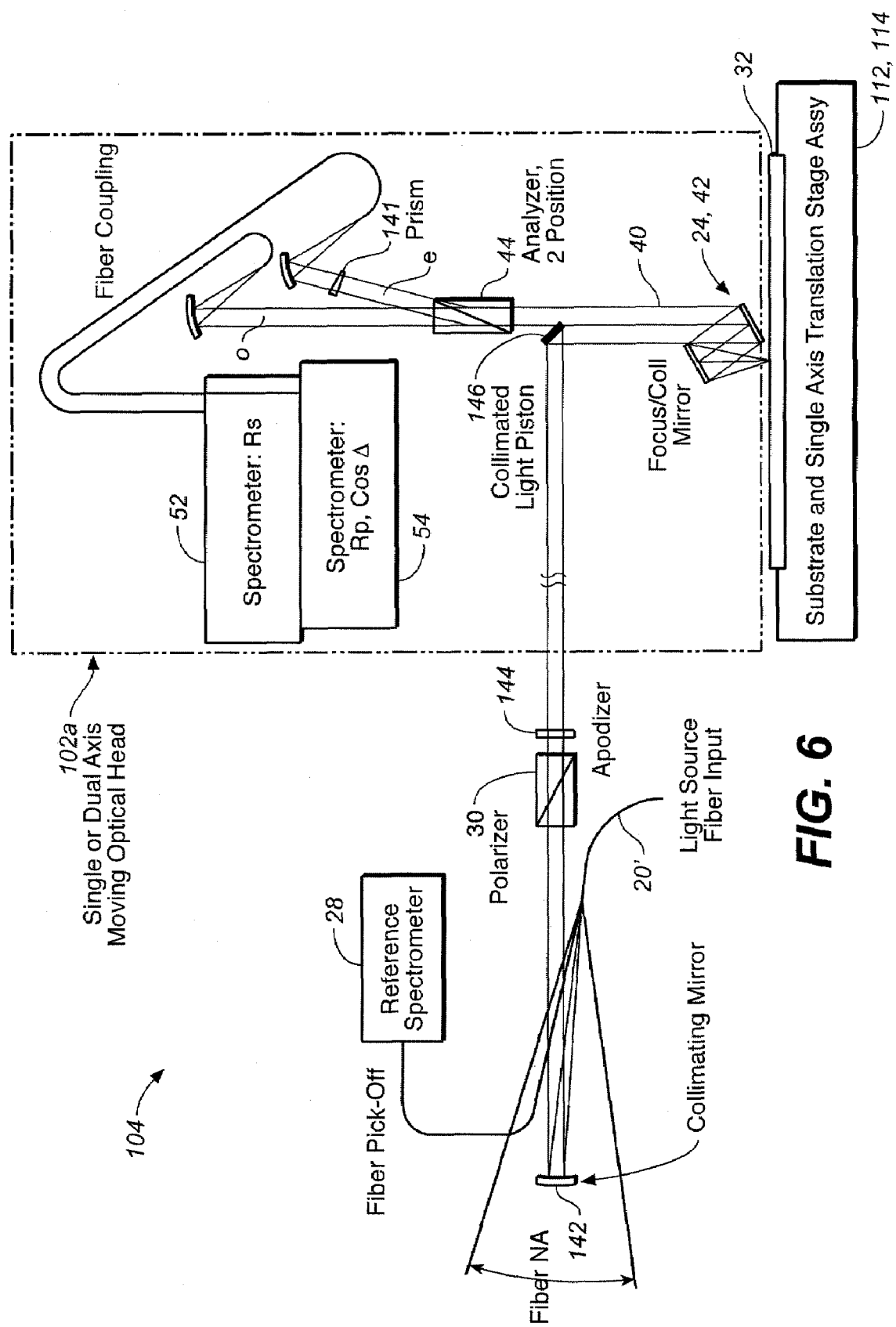
FIG. 6 is a schematic diagram of an apparatus illustrating in more detail the components in the optics head in FIGS. 4A, 4C.

FIG. 6 is a block diagram of an optical arrangement 140 illustrating a practical implementation for the optics head 102 of FIGS. 4A, 4C. As shown in FIG. 6, the optics head 102a contains an optical arrangement similar to that in FIG. 1A, where the analyzer 44 splits the collected beam 40 into an o-ray directed to spectrometer 54 and an e-ray directed to spectrometer 52 through a prism 141, which compensates for the dispersion caused by the analyzer 44 for the deviated beam. The light from light source is conveyed through an optical fiber 20' and reflected by a collimating mirror 142 to polarizer 30 and apodizer 144 in a collimated light piston to optics head 102a. In optics head 102a, the light is reflected by mirror 146 to the beam shaping optics 24, 42 comprising two focus/collimating mirrors to sample 32. The same focus/collimating mirrors 24/42 collect light reflected by sample 32 to analyzer 44. As will be noted from FIG. 6, collimating or focusing mirrors are used for directing and focusing radiation from the light source cross the sample 32 and for collecting light reflected by the sample towards the analyzer. By using mirrors for such purposes, chromatic aberration is reduced, especially where the detection employs radiation over a wide range of wavelengths, such as 150 nanometers to 1,000 nanometers.

Figure 7:
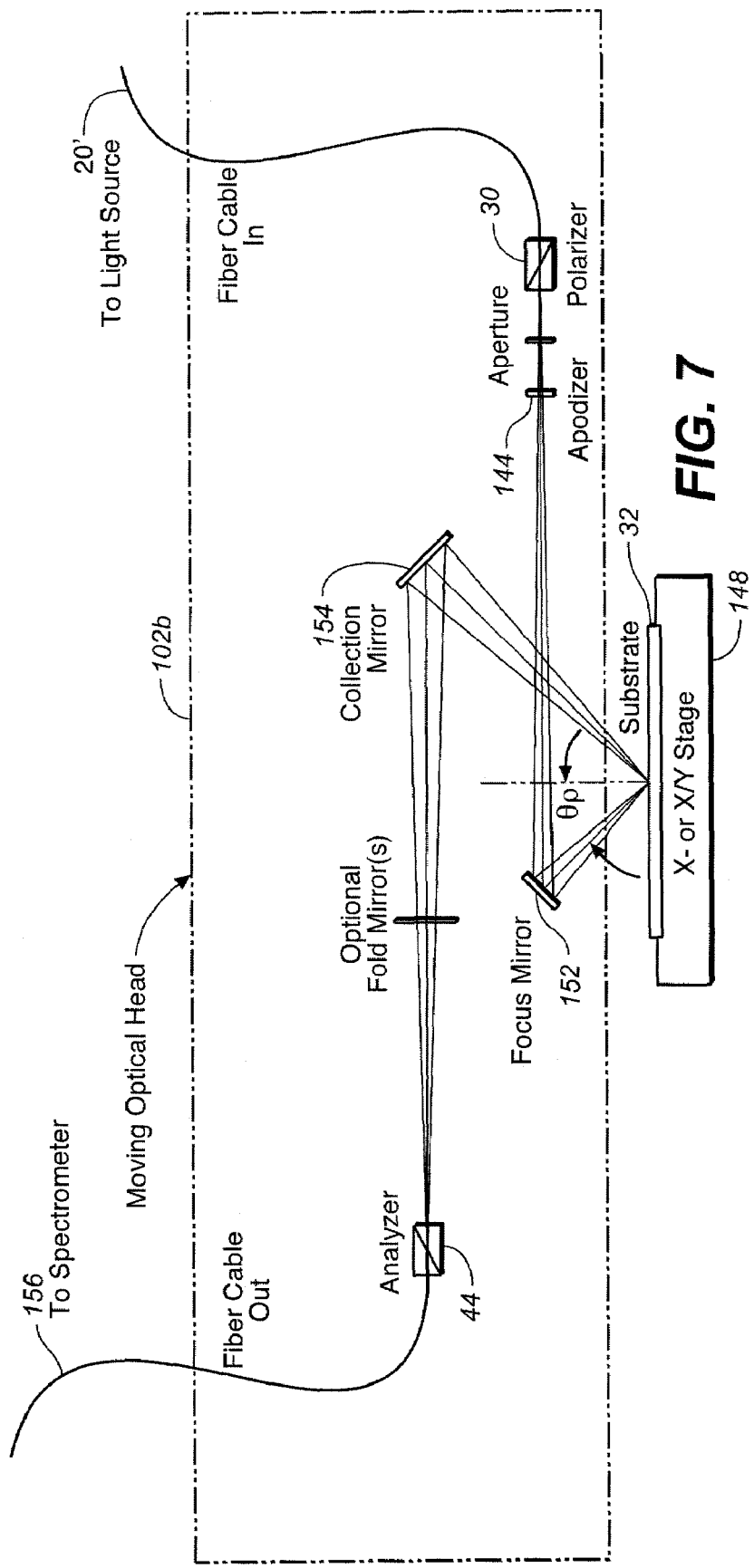
FIG. 7 is a schematic view of an apparatus for measuring periodic structures illustrating in more detail an alternative construction of the optics head in FIGS. 4A, 4C.

FIG. 7 is a schematic view of another alternative construction 102b of the optics head in FIGS. 4A, 4C. As shown on FIG. 7, optics head 102b includes an optical fiber 20' conveying radiation from a radiation source (not shown) through polarizer 30 and apodizer 144 and focused by mirror 152 to sample 32. Sample 32 is moved by a stage 148 along one direction (x) or along two transverse (x/y) directions. Radiation reflected by sample 32 is collected by collection mirror 154 and focused to an analyzer 44. The radiation that passes the analyzer is conveyed to a spectrometer (not shown) by fiber 156. Analyzer 44 is rotated to desirable positions as described above in reference to FIG. 2.

Figure 8:
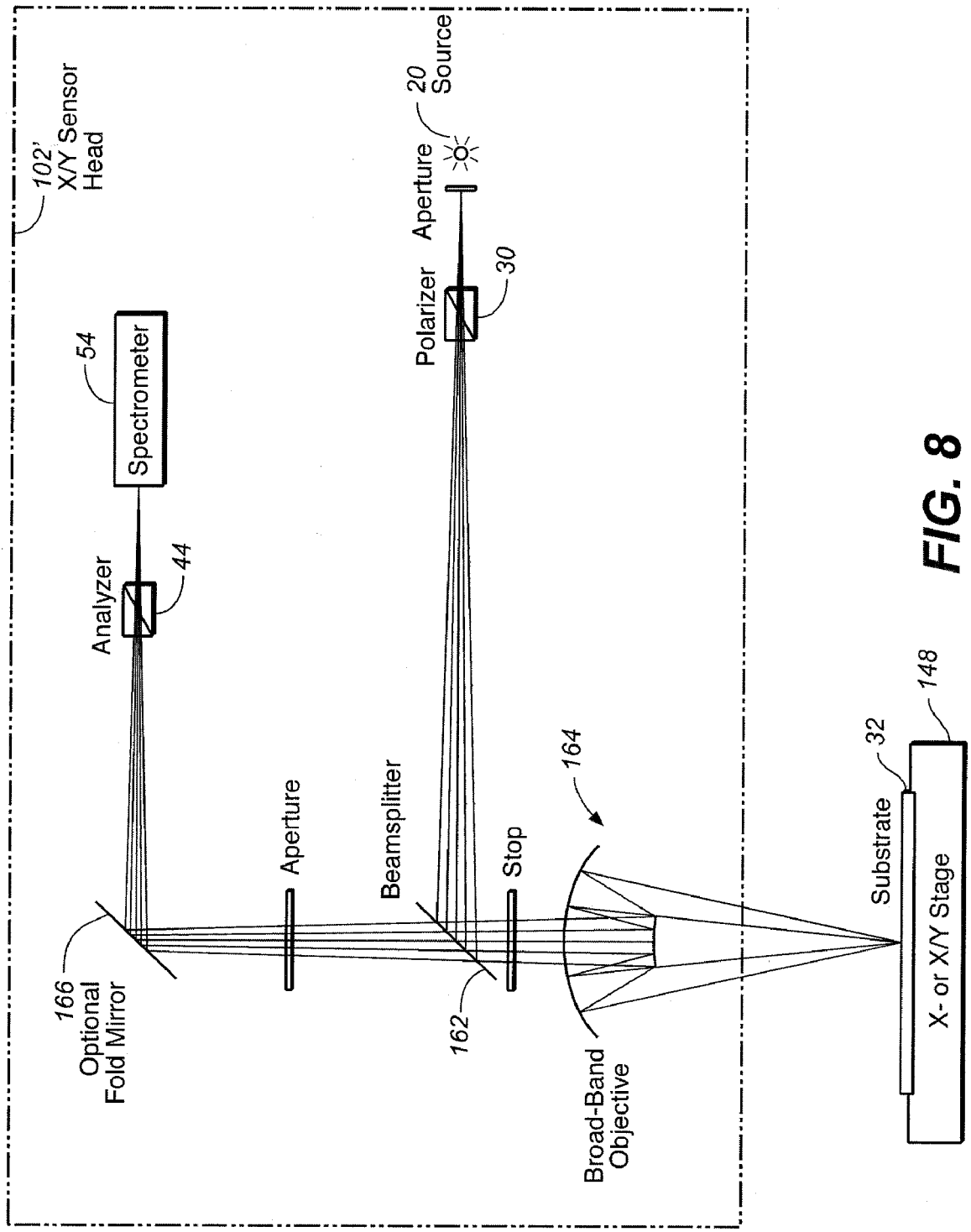
FIG. 8 is a schematic view of the different components in the optics head to illustrate in more detail the optics head of FIGS. 4B, 5.

FIG. 8 is a schematic view of the different components in the optics head 102' to illustrate in more detail the optics head of FIGS. 4B, 5. As shown in FIG. 8, optics head 102' includes radiation source 20 which supplies a beam of radiation that passes polarizer 30 and is reflected by a beam splitter 162 and focused by a broadband objective 164 to wafer 32. The reflected radiation from the wafer is collected by objective 164, passed through beam splitter 162 and reflected by mirror 166 to analyzer 44 to spectrometer 54. Preferably the analyzer 44 is rotated so that its plane of polarization and the plane of polarization of the polarizer 30 are as described above in reference to FIG. 2.

Figure 9:
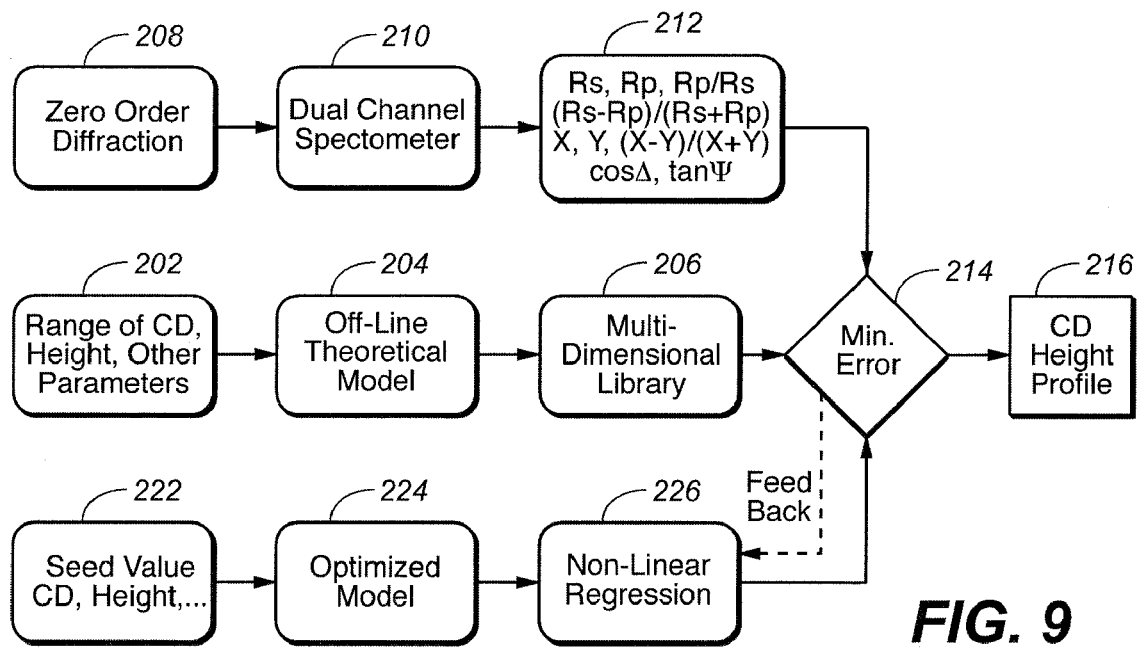
FIG. 9 is a flowchart illustrating the operation of the apparatuses of FIGS. 1A, 1C and 2.

The process for deriving one or more parameters of the periodic structure using a computer such as computer 60 will now be described in reference to FIG. 9 which is a flowchart illustrating the operation of apparatuses of FIGS. 1A, 1B and 2. First, one obtains the possible range of values of the one or more parameters of the periodic structure, such as critical dimension (CD), height (H), sidewall angle (SWA) and other parameters (block 202). A theoretical model is then constructed (block 204) and a multi-dimensional library is constructed (block 206).

One of the apparatuses of FIGS. 1A, 1C and 2 is then utilized to obtain a measurement of the zeroth order diffraction of the periodic structure in the manner described above (block 208), where such diffraction is detected by a single or dual channel spectrometer as described above (block 210). As described above, the quantities $R_s$, $R_p$ and X, Y may be measured directly using the apparatuses of FIGS. 1A, 1C and 2. From these four quantities, other radiation parameters may be derived in the manner described above (block 212). The multi-dimensional library 206 constructed is then utilized and comparison is made between spectra in the library and the measured data from block 212. The parameters of the model are varied (block 206) in order to minimize the error between the spectra corresponding to the predicted values of the parameters of the periodic structure according to the model, and the measured spectra from block 212 in order to arrive at the actual values of the parameters of the periodic structure, such as CD, height and sidewall angle (diamond 214).

Alternatively, instead of using a multi-dimensional library, a non-linear optimization (e.g. non-linear regression) algorithm may be employed instead. For this purpose, the initial or seed values of the parameters of the periodic structure are obtained (block 222). An optimization model is constructed (block 224) and a non-linear regression algorithm (block 226) is employed with feedback (diamond 214) to again minimize the error between the spectra of radiation parameters corresponding to the predicted values of the parameters of the periodic structure and the measured spectra from block 212 in order to arrive at the actual values of parameters such as CD, height and sidewall angle (block 216).

Figure 10:
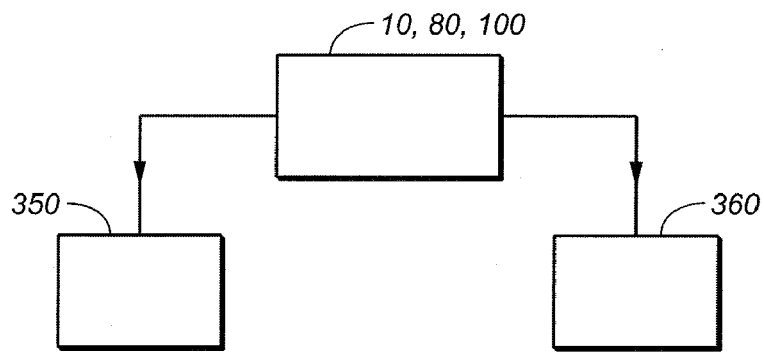
FIG. 10 is a schematic block diagram illustrating a wafer processing apparatus including a track/stepper and an etcher and a spectroscopic measurement device where information from a periodic structure and/or associated structures from the device as used to control the manufacturing process and the track, stepper and/or etcher to illustrate the invention.

FIG. 10 is a block diagram of an integrated diffraction-based metrology system, a photolithographic track/stepper and an etcher to illustrate another aspect of the invention. A layer of material such as photoresist is formed on the surface of a semiconductor wafer by means of track/stepper 350, where the photoresist forms a grating structure on the wafer. One or more of the CD, H, SWA and/or other parameters of the grating structure are then measured using systems 10, 80, 100 of FIGS. 1A, 1C and 2, and one or more of the above-described techniques may be employed if desired to find the value(s) of the one or more parameters of the photoresist pattern. Such value(s) from the computer 60 are then fed back to the track/stepper 350, where such information may be used to alter the lithographic process in track/stepper 350 to correct any errors. In semiconductor processing, after a layer of photoresist has been formed on the wafer, an etching process may be performed, such as by means of etcher 360. The layer of photoresist is then removed in a manner known in the art and the resulting grating structure made of semiconductor material on the wafer may again be measured if desired using system 10, 80 or 100. The value(s) measured using any one or more of the above-described techniques may be supplied to the etcher for altering any one of the etching parameters in order to correct any errors that have been found using system 10, 80 or 100. Of course the results obtained by one or more of the above described techniques in system 10, 80 or 100 may be used in both the track/stepper and the etcher, or in either the track/stepper or the etcher but not both. The track/stepper 350 and/or etcher 360 may form an integrated single tool with the system 10, 80 or 100 for finding the one or more parameters of a periodic structure, or may be separate instruments from it.

Figure 11:
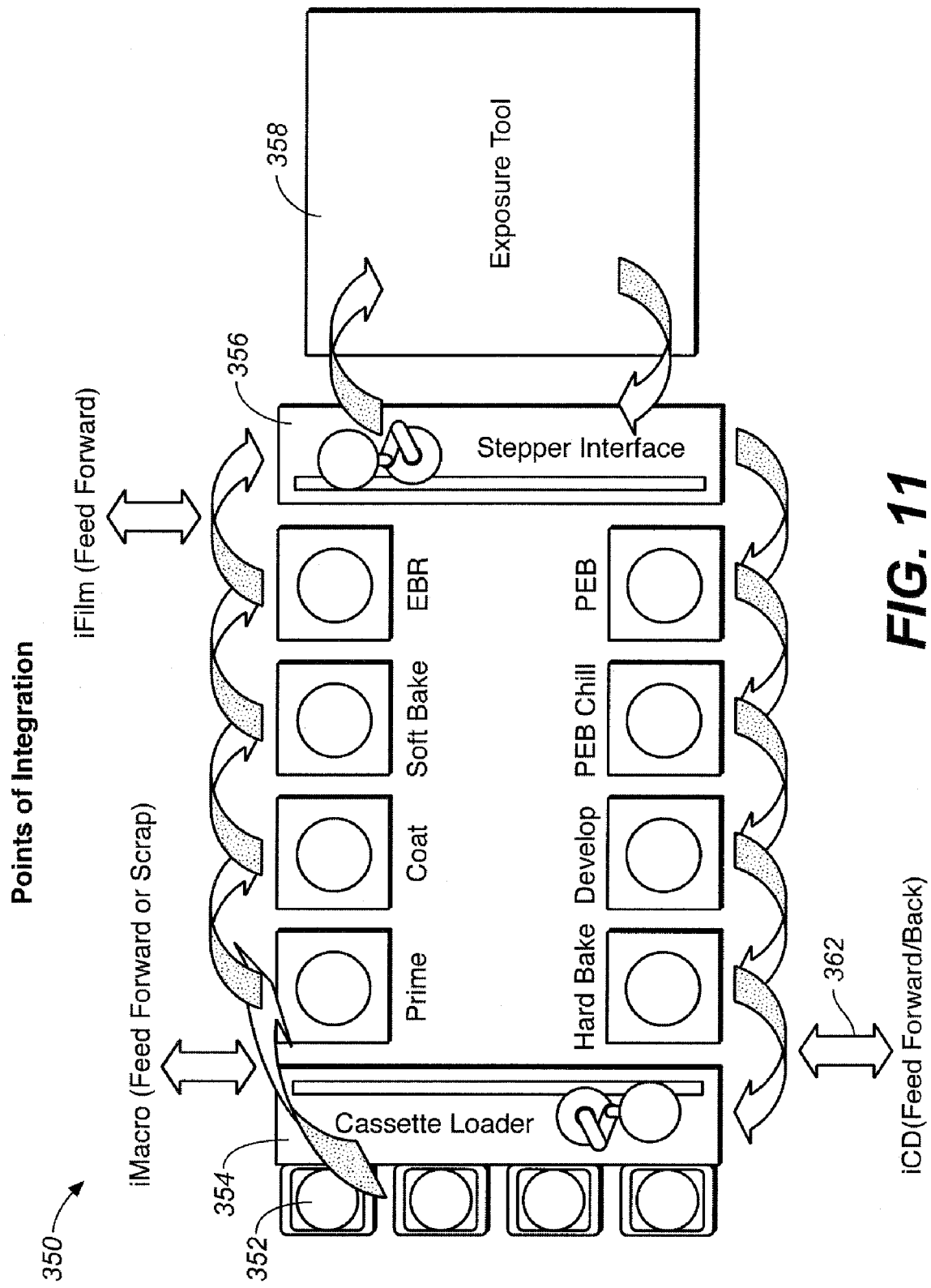
FIG. 11 is a schematic block diagram and flowchart illustrating in more detail the track/stepper of FIG. 7.

FIG. 11 is a schematic view of the track/stepper 350 and an associated flowchart illustrating a process for semiconductor wafer processing to illustrate in more detail the points of integration of the processing process with the detection of profiles of periodic structures and associated films to illustrate in more detail a part of the process in FIG. 10. As shown in FIG. 11, a semiconductor wafer 352 may be loaded from a cassette loader 354 to several stations labeled "prime," "coat," "soft bake," "EBR" etc. Then the wafer 352 is delivered by a stepper interface 356 to exposure tool 358. The different processes at the four locations mentioned above are set forth below:

At the location "Prime", the wafer undergoes chemical treatment before a layer of photoresist is spun on it, so that the photoresist layer can stick to wafer. At the location "Coat", a layer of photoresist coating is spun onto the wafer. At "Soft bake", the layer of resist is baked to remove chemical solvent from the resist. At "EBR" which stands for "edge-bead removal", a solvent nozzle or laser is used to remove excess photoresist from the edge of wafer.

After the wafer has been exposed to radiation by tool 358, the wafer then undergoes four additional processes: "PEB," "PEB chill," "Develop," and "Hard bake." At "PEB or post exposure bake", the wafer is baked to reduce standing-wave effect from the exposure tool. Then it is cooled at "PEB chill". The wafer is then washed with reagent to develop the photoresist, so that un-exposed (negative) or exposed (positive) photoresist is removed. The wafer then is baked at "Hard bake" to stabilize the photoresist pattern. It will be noted that all of the components of device 350 of FIG. 8 except for the "exposure tool" 358 is known as the "Track" (also called cluster).

After these latter four processes have been completed, the wafer 352 is then returned to the cassette loader 354 and this completes the processing involving the stepper 350. The detection system 10, 80 or 100 may be applied at arrow 362 to measure the parameters of the periodic structure and associated film(s). Thus, such parameters may be measured after "hard bake."

While the invention has been described above by reference to various embodiments, it will be understood that changes and modifications may be made without departing from the scope of the invention, which is to be defined only by the appended claims and their equivalents. All references referred to herein are incorporated by reference in their entirety.

What is claimed is:

1. An apparatus for measuring one or more parameters of a periodic structure of a sample, comprising:

an optical device directing a polychromatic beam of electromagnetic radiation to the structure in a plane of incidence and passing and collecting radiation from the beam after it has been modified by the structure;

said optical device having a plane of polarization that is rotated relative to the periodic structure;

at least one detector detecting the collected radiation to provide at least one output when the plane of polarization is at each of a plurality of different angles to the periodic structure; and a processing system processing said sample, said processing system responsive to the at least one output for adjusting a processing parameter.

2. The apparatus of claim 1, said plurality of different angles having values different from 0, 90, 180, 270 degrees.

3. The apparatus of claim 2, wherein said plurality of different angles include one or more of 0, 45, 90, 135, 180, 225, 270 and 315 degrees to the plane of incidence.

4. The apparatus of claim 1, wherein the device divides the radiation from the beam after it has been modified by the structure into an ordinary ray and an extraordinary ray, said two rays having substantially orthogonal polarizations, said apparatus further comprising two detectors, each of the two detectors detecting a corresponding one of the two rays.

5. The apparatus of claim 1, said device comprising a first element directing the polychromatic beam of electromagnetic radiation to the structure and a second element collecting radiation from the beam after it has been modified by the structure, wherein each of said two elements has a numerical aperture, and wherein the numerical aperture of the second element is smaller than that of the first.

6. The apparatus of claim 1, further comprising a processor deriving the one or more parameters from the at least one output.

7. The apparatus of claim 6, wherein the processor derives a critical dimension, height or sidewall angle of the structure.

8. The apparatus of claim 1, wherein said polychromatic beam of electromagnetic radiation is at an oblique angle to a plane of the structure.

9. The apparatus of claim 1, further comprising an optical objective that focuses said polychromatic beam of electromagnetic radiation to the structure, and focuses the collected radiation from the beam after it has been modified by the structure.

10. The apparatus of claim 1, wherein said polychromatic beam of electromagnetic radiation to the structure is unpolarized.

11. A method for measuring one or more parameters of a periodic structure of a sample, comprising:
    directing a polychromatic beam of electromagnetic radiation to the structure in a plane of incidence;
    rotating relative to the periodic structure an optical device having a plane of polarization;
    passing and collecting radiation from the beam after it has been modified by the structure by means of the optical device;
    detecting the collected radiation to provide at least one output when the plane of polarization is at each of a plurality of different angles to the periodic structure; and
    using the at least one output to adjust a processing parameter of a processing machine for processing said sample.

12. The method of claim 11, said plurality of different having values different from 0, 90, 180, 270 degrees.

13. The method of claim 12, wherein said plurality of different angles include one or more of 0, 45, 90, 135, 180, 225, 270 and 315 degrees to the plane of incidence.

14. The method of claim 11, further comprising dividing the radiation from the beam after it has been modified by the structure into an ordinary ray and an extraordinary ray, said two rays having substantially orthogonal polarizations, said method further comprising employing two detectors to detect the two rays, with each of the two detectors detecting a corresponding one of the two rays.

15. The method of claim 11, further comprising deriving the one or more parameters from the at least one output.

16. The method of claim 11, wherein said directing directs the polychromatic beam of electromagnetic radiation to the structure at an oblique angle to a plane of the structure.

17. The method of claim 11, further comprising using an optical objective to focus said polychromatic beam of electromagnetic radiation to the structure, and to focus the collected radiation from the beam after it has been modified by the structure.

* * * * *